United States Patent
Gerber et al.

(10) Patent No.: US 7,585,271 B2
(45) Date of Patent: Sep. 8, 2009

(54) IMPLANTABLE DEVICES AND METHODS FOR TREATING URINARY INCONTINENCE

(75) Inventors: Martin T. Gerber, Maple Grove, MN (US); Warren L. Starkebaum, Plymouth, MN (US); John M. Swoyer, Andover, MN (US)

(73) Assignee: THD SpA, Correggio (IT)

( * ) Notice: Subject to any disclaimer, the term of this patent is extended or adjusted under 35 U.S.C. 154(b) by 565 days.

(21) Appl. No.: 10/698,131

(22) Filed: Nov. 1, 2003

(65) Prior Publication Data
US 2005/0096751 A1 May 5, 2005

(51) Int. Cl.
*A61F 2/02* (2006.01)
(52) U.S. Cl. .......................................... 600/30
(58) Field of Classification Search .............. 600/29–32; 128/DIG. 25, 897–898
See application file for complete search history.

(56) References Cited

U.S. PATENT DOCUMENTS

| | | | |
|---|---|---|---|
| 4,979,947 A | 12/1990 | Berman | |
| 5,489,300 A | 2/1996 | Capecchi et al. | |
| 5,542,799 A | 8/1996 | Culpen | |
| 5,599,852 A * | 2/1997 | Scopelianos et al. | 523/105 |
| 5,704,893 A | 1/1998 | Timm | |
| 5,741,104 A | 4/1998 | Lat et al. | |
| 5,792,478 A | 8/1998 | Lawin et al. | |
| 5,824,086 A | 10/1998 | Silvestrini | |
| 5,964,806 A * | 10/1999 | Cook et al. | 623/11.11 |
| 6,090,063 A | 7/2000 | Makower et al. | |
| 6,098,629 A | 8/2000 | Johnson et al. | |
| 6,190,684 B1 | 2/2001 | Hench et al. | |
| 6,231,613 B1 | 5/2001 | Greff et al. | |
| 6,251,063 B1 | 6/2001 | Silverman et al. | |
| 6,277,392 B1 | 8/2001 | Klein | |
| 6,335,028 B1 * | 1/2002 | Vogel et al. | 424/422 |
| 6,338,345 B1 | 1/2002 | Johnson | |
| 6,354,991 B1 | 3/2002 | Gross et al. | |
| 6,358,197 B1 | 3/2002 | Silverman et al. | |
| 6,401,718 B1 | 6/2002 | Johnson et al. | |
| 6,491,623 B2 | 12/2002 | Snyder et al. | |
| 6,533,717 B2 | 3/2003 | Silverman et al. | |
| 6,579,224 B1 | 6/2003 | Burton et al. | |
| 6,591,838 B2 * | 7/2003 | Durgin | 128/898 |
| 6,592,859 B1 | 7/2003 | Bley | |
| 6,595,910 B2 | 7/2003 | Silverman et al. | |
| 6,652,883 B2 * | 11/2003 | Goupil et al. | 424/489 |

(Continued)

FOREIGN PATENT DOCUMENTS

WO    02/11696    2/2002

(Continued)

*Primary Examiner*—John P Lacyk
(74) *Attorney, Agent, or Firm*—Pearne & Gordon LLP

(57) ABSTRACT

In general, the invention is directed to treatment of urinary incontinence by the implantation of one or more bulking prostheses proximate to a urethral sphincter. These bulking prostheses, which may include biocompatible hydrogel, are implanted into the tissue outside the urethra, proximate to a urethral sphincter. When implanted, the bulking prostheses are in a miniature state. Upon introduction into the body, the devices enter an enlarged state. In their enlarged state, the bulking prostheses supply extra bulk to the tissues proximate to the external urethral sphincter. With the extra bulk, the patient can exercise voluntary control over the external urethral sphincter to close or maintain closure of the urethra and maintain urinary continence.

13 Claims, 6 Drawing Sheets

U.S. PATENT DOCUMENTS

| | | |
|---|---|---|
| 7,049,346 B1 | 5/2006 | Van Bladel et al. |
| 2001/0010021 A1 | 7/2001 | Boyd et al. |
| 2001/0046518 A1 | 11/2001 | Sawhney |
| 2002/0019579 A1 | 2/2002 | Silverman |
| 2002/0072720 A1 | 6/2002 | Hague et al. |
| 2002/0091295 A1 | 7/2002 | Wilk |
| 2002/0188308 A1 | 12/2002 | Tu et al. |
| 2003/0018344 A1 | 1/2003 | Kaji |
| 2004/0247867 A1 * | 12/2004 | Chaouk et al. .............. 428/364 |
| 2005/0096497 A1 | 5/2005 | Gerber et al. |
| 2005/0096751 A1 | 5/2005 | Gerber et al. |

FOREIGN PATENT DOCUMENTS

| | | |
|---|---|---|
| WO | 02/32321 | 4/2002 |

* cited by examiner

IMPLANTABLE DEVICES AND METHODS FOR TREATING URINARY INCONTINENCE

FIELD OF THE INVENTION

The invention relates to medical devices implantable in and near the genitourinary tract.

BACKGROUND

Urinary incontinence is the loss of voluntary control to retain urine. Urinary incontinence may be the result of a number of causes, such as old age, disease, pregnancy or trauma. Some patients, especially women, may experience urinary incontinence during stressful events, such as sneezing, laughing, coughing, lifting, or other activity that puts pressure on the bladder.

Some patients suffering from urinary incontinence may deal with the condition by conservative measures, such as performing exercises to strengthen the outer urethral sphincter. For some patients, however, such conservative measures are ineffective. In a healthy human being, the internal and external urethral sphincters contract to prevent the escape of urine, the external sphincter being under the voluntary control of the patient. In some patients, however, the patient may have some control over the external sphincter, but one or both sphincters lack sufficient bulk to maintain closure of the urethra and prevent the escape of urine.

There have been many approaches addressing urinary incontinence. Some approaches manage urine that has been released, but other approaches seek to help the patient prevent release by electrical and/or mechanical processes. U.S. Pat. No. 6,354,991 to Gross, for example, describes a system that uses electrodes to detect abdominal stress and to stimulate muscles associated with urine control. Other approaches have involved augmentation of tissues that allow the patient to resist urine flow. U.S. Pat. No. 6,277,392 to Klein, for example, discloses an injectable augmentation composition. U.S. Pat. No. 6,592,859 to Bley describes small solid polymer particles that are injected into tissue and swell following implantation.

Table 1 below lists documents that disclose some of the many techniques for addressing urinary incontinence.

TABLE 1

| Patent Number | Inventors | Title |
| --- | --- | --- |
| 6,635,037 | Bennett | Male Urinary Incontinence Device |
| 6,605,097 | Lehe et al. | Apparatus and Method for Treating Female Urinary Incontinence |
| 6,592,859 | Bley | Controlled expansion Sphincter Augmentation Media |
| 6,354,991 | Gross et al. | Incontinence Treatment Device |
| 6,277,392 | Klein | Tissue Injectable Composition |
| 6,231,613 | Greff et al. | Methods for Soft Tissue Augmentation in Mammals |

All documents listed in Table 1 above are hereby incorporated by reference herein in their respective entireties. As those of ordinary skill in the art will appreciate readily upon reading the Summary of the Invention, Detailed Description of the Preferred Embodiments and Claims set forth below, many of the devices and methods disclosed in the patents of Table 1 may be modified advantageously by using the techniques of the present invention.

SUMMARY OF THE INVENTION

The present invention is directed to devices and methods for addressing urinary incontinence. The invention has certain objects. That is, various embodiments of the present invention provide solutions to one or more problems existing in the prior art with respect to addressing urinary incontinence. The problems include, for example, effectiveness of the treatment, inconvenience to the patient, the invasiveness of surgery that may be required along with the associated recovery time, and risks associated with mechanical or electrical failure of implanted devices having moving parts or electrical components. In the case of some implanted materials or devices, there are risks associated with device migration, and the implanted materials or devices are not easily removable.

Various embodiments of the present invention have the object of solving at least one of the foregoing problems. In general, the invention provides for treatment of urinary incontinence by the implantation of one or more bulking prostheses proximate to a urethral sphincter. These bulking prostheses are implanted into the tissues outside the urethra. In some embodiments, the bulking prostheses are implanted into the tissue directly, and in other embodiments, bulking prostheses are inserted through a hole in the urethral wall. One exemplary procedure for delivering the devices is via a syringe. Another exemplary procedure involves drawing the urethral wall into a cavity of a device, forming a hole in the urethral wall, and inserting one or more bulking prostheses through the hole into the surrounding tissue.

When implanted, the bulking prostheses are in a miniature state. Upon introduction into the body, the bulking prostheses enter an enlarged state. In their enlarged state, the bulking prostheses supply extra bulk to the tissues proximate to the external urethral sphincter. With the extra bulk, the patient can exercise voluntary control over the external urethral sphincter to close the urethra and maintain urinary continence. Bulking prostheses that include a biocompatible hydrogel material, for example, assume a miniature state for implantation, and upon implantation absorb the fluids of the body to assume an enlarged state. Bulking prostheses in the enlarged state may assume any number of shapes, such as capsule-shaped, cylindrical, spherical, egg-shaped, or a partial cylinder.

The invention includes embodiments directed to a method comprising implanting one or more bulking prosthesis with an apparatus that applies vacuum pressure as part of the implantation. The invention also includes embodiments directed to a system that can perform implantation with a vacuum. The invention further encompasses embodiments comprising a bulking prosthesis having a partial cylinder shape.

Various embodiments of the invention may possess one or more features capable of fulfilling the objects outlined above. The various embodiments of the invention provides for less invasive surgical intervention than other surgical techniques. As a result, the implantations may be performed in less time and with less expense, and with reduced recovery time for the patient. In addition, bulking prostheses implanted according to the invention may be readily removed, if necessary. Also, once the implants are in place, no further maintenance is necessary, as the bulking prosthesis require no electrical power supply and have no coupled moving parts. The techniques of the invention further allow implantation of comparatively large bulking prostheses, which tend to stay in one piece and which ten not to migrate from the site of implantation.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1:
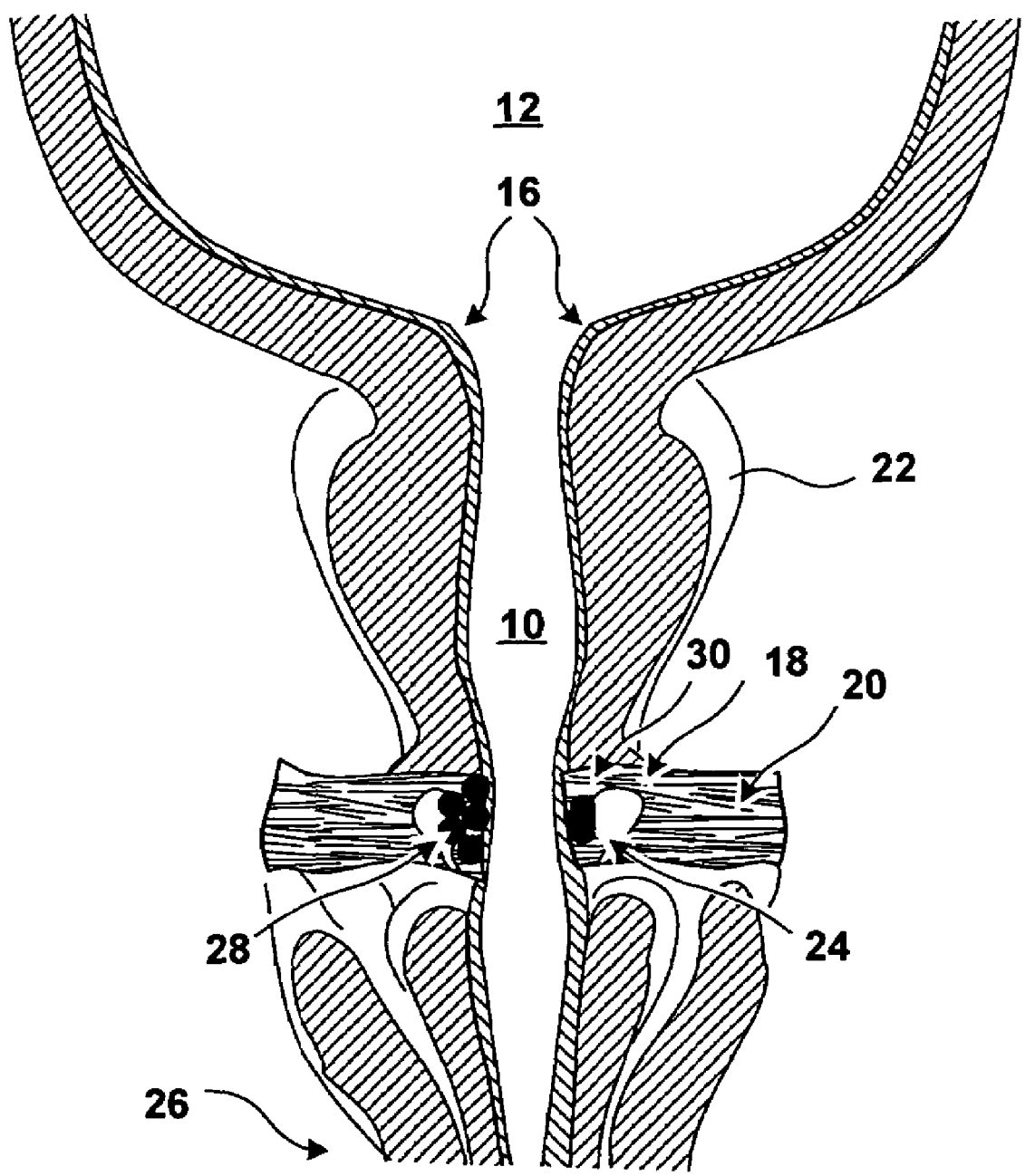
FIG. 1 is a coronal cross section of anatomical structures surrounding a urethra of a male patient, showing an exemplary placement of bulking prostheses.

FIG. 1 is a coronal cross section of anatomical structures surrounding a urethra 10 of a male patient. Urethra 10 is a tube, including a wall and a lumen, that extends from the urinary bladder 12 to an external urethral orifice (not shown in FIG. 1). Flow of urine from bladder 12 and through urethra 14 is controlled by an internal urinary sphincter 16 and an external urinary sphincter 18. Internal urinary sphincter 16 is not really a separate muscle, but is a portion of bladder 12 that operates as a sphincter. Internal urinary sphincter 16 is not under voluntary control of the patient.

External urinary sphincter 18 is further away from bladder 12 than internal urinary sphincter 16. External urinary sphincter 18 encircles urethra 10 and is reinforced by the pelvic diaphragm 20. Contraction and relaxation of external urinary sphincter 18 is under the voluntary control of the patient.

These properties of the external urinary sphincter are true in women as well as in men, but in men, the prostate 22 encircling urethra 10 is interposed between bladder 12 and pelvic diaphragm 20. In addition, men have bulbourethral glands 24 proximate to pelvic diaphragm 20, and women do not. Furthermore, a man's urethra is typically much longer than a woman's urethra, because the urethra of a man traverses the penis 26.

FIG. 1 shows two of many possible deployments of bulking prostheses 28, 30 implanted proximate to external urinary sphincter 18. Bulking prostheses 28 comprises a plurality of spherical prostheses implanted in a region of tissue outside urethra 10 and proximate to external urinary sphincter 18. Bulking prosthesis 30 comprises a single capsule-shaped or substantially cylindrical device implanted in a region of tissue outside urethra 10 and proximate to external urinary sphincter 18. Although FIG. 1 shows deployment of both spherical prostheses and capsule-shaped prosthesis, a physician may prefer to implant prostheses of a single configuration.

The patient benefits from bulking prostheses 28, 30 by being enabled to voluntarily control containment and release of urine. In the absence of bulking prostheses 28, 30, a physical deficit causes the patient to experience urinary incontinence. The deficit may be caused by old age, disease, trauma or another cause. In women, pregnancy can lead to urinary incontinence. Although the patient retains some control over external urethral sphincter 18, the patient is unable to control containment and release of urine in a reliable manner. In some patients, urinary incontinence may be a problem when stressful events, such as sneezing, laughing, coughing, lifting, or other physical activity, puts pressure on bladder. Women are especially vulnerable to stress-related urinary incontinence. With bulking prostheses 28, 30 implanted outside urethra 10 proximate to external urinary sphincter 18, however, the patient has more bulk proximate to urethra 10, and is therefore able to exercise voluntary control over the external urethral sphincter 18 to close urethra 10.

When implanted, bulking prostheses 28, 30 were in a miniature state. Over time, bulking prostheses 28, 30 swelled to an enlarged state. A bulking prosthesis may include a biocompatible hydrogel material that, in the inert state free and of moisture, can be compressed into a miniature state. When placed in the body of a patient, however, the hydrogel absorbs fluid from the body of the patient and swells to an enlarged state.

In particular, the bulking prosthesis in the miniature state comprises a substantially solid unhydraded hydrophilic polymer. Following implantation into the body of patient 10, however, the polymer absorbs water from the body of patient 10 to expand into an enlarged form and to form a colloidal gel in which the absorbed water is the dispersion medium. The bulking prosthesis may be formed from any of several biocompatible hydrogel materials, such as a multi-block polyacrylonitrile-based hydrogel material. Such a material, is commercially available as HYPAN™ from Lipo Chemicals, Inc. The bulking prosthesis may also include a radiopaque material, such as tantalum, to make the bulking prosthesis visible on an X-ray. Other radiopaque materials include barium sulfate, platinum or tungsten.

A bulking prostheses may be any number of shapes, in addition to the capsule shape spherical shape described above. Other shapes for a bulking prostheses will be described below.

Figure 2:
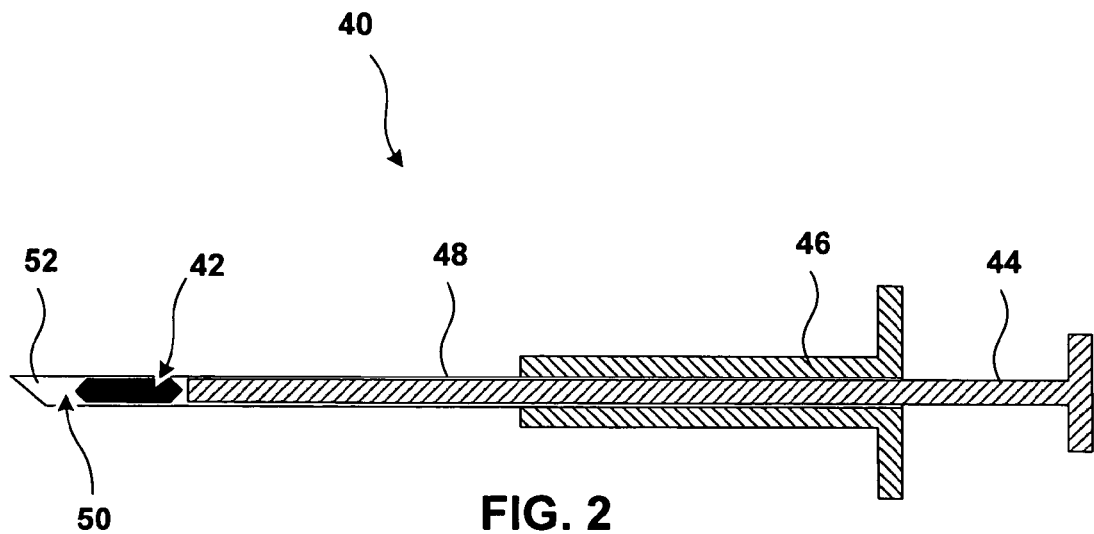
FIG. 2 is a cross section of an exemplary syringe that may be used to practice the invention.

FIG. 2 is a cross-sectional diagram of a device 40 that can implant a bulking prosthesis 42. Device 40 comprises a syringe, which includes a plunger member 44, a body member 46 and a hollow needle 48 having a lumen 50. Needle 48 is fixedly coupled to body member 46, while plunger member 44 is free to move in lumen 50. Lumen 50 of needle 48 has been enlarged to show bulking prosthesis 42, in a miniature state, disposed in lumen 50.

Distal end 52 of needle 48 includes a sharp point that can pierce tissue such as the wall of a urethra or tissue surrounding a urethra. Distal end 52 further includes an opening through which bulking prosthesis 42 may be expelled from lumen 50 by depressing plunger member 44 with respect to body member 46.

Figure 3:
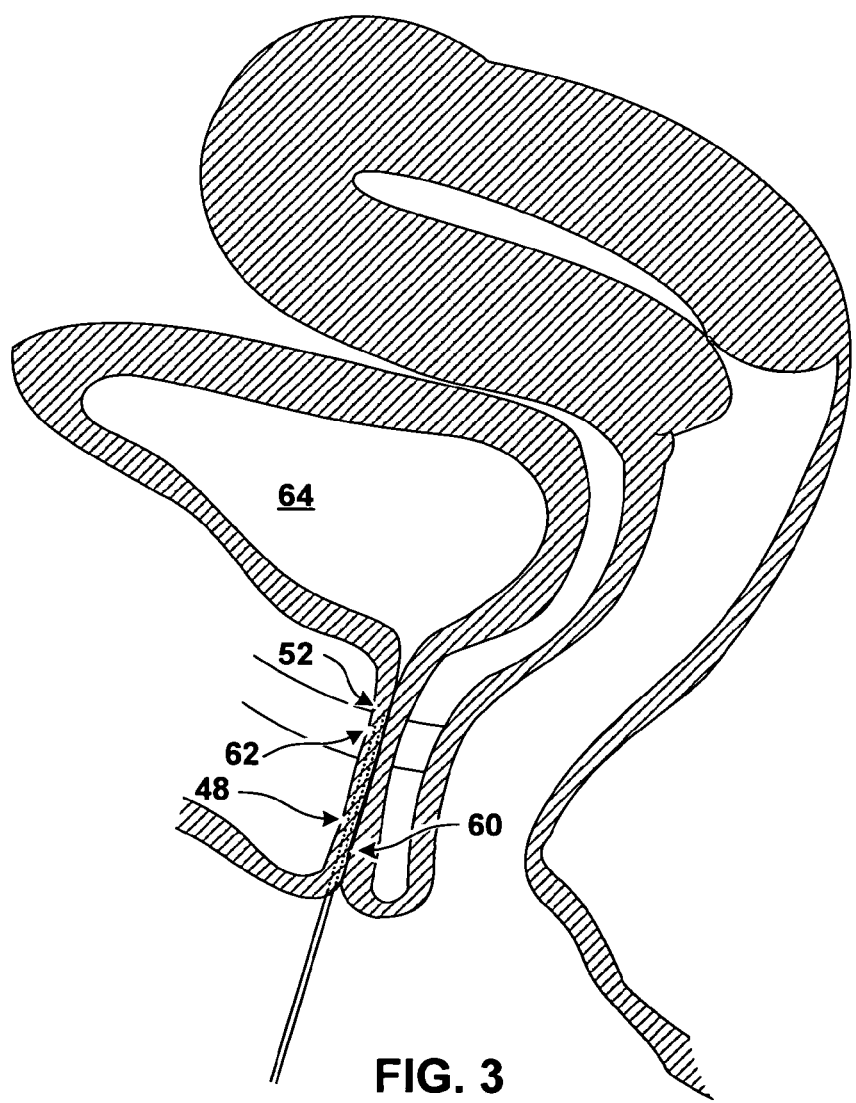
FIG. 3 is a sagittal cross section of genitourinary region of a female patient, showing a technique for implantation of a bulking prosthesis with a needle such as the needle shown in FIG. 2.

FIG. 3 is a sagittal cross-section of the genitourinary region of a female patient, showing a technique for implantation of a bulking prosthesis with a needle such as needle 48 shown in FIG. 2. With the patient under general or local anesthesia, a physician inserts the needle 48 substantially parallel to urethra 60 until distal end 52 is proximate to the external urethral sphincter 62. By depressing a plunger, the physician can expel one or more bulking prostheses (not shown in FIG. 3) in a miniature state from distal end 52 of needle 48.

As an alternative to the technique shown in FIG. 3, a physician may traverse the lumen of urethra 60 with needle 48, then penetrate the urethral wall to implant bulking prosthesis in the tissues outside urethra 60 and proximate to the external urethral sphincter 62.

The technique depicted in FIG. 3 is less likely to be suitable for a man. In women, urethra 60 is relatively short and external urethral sphincter 62 is not a deep structure. Needle 48 may be marked to assist the surgeon with the depth of implantation, and to prevent inadvertent puncturing of the bladder 64. In men, however, the depth of external urethral sphincter 18 may make this implantation technique impractical.

Figure 4:
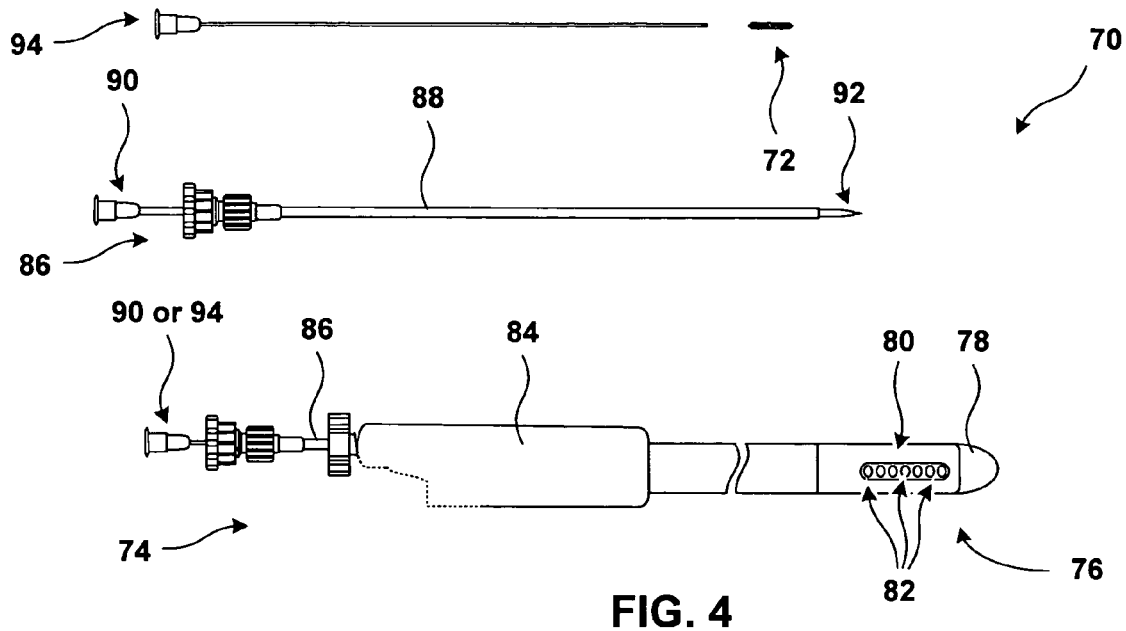
FIG. 4 is a plan view of components of a delivery apparatus that may be used to practice the invention.

FIG. 4 shows components of a delivery apparatus 70 that may be used to implant a bulking prosthesis 72 proximate to an external urethral sphincter. Although delivery apparatus 70 supports implantation in men, the same apparatus may also be used to implant bulking prostheses in women.

Delivery apparatus 70 is embodied as an endoscopic device such as a cystoscope. In one embodiment, delivery apparatus 70 comprises a scaled down Gatekeeper™ device commercially available from Medtronic, Inc., sized to traverse the urethra. Delivery apparatus 70 includes an endoscopic member 74 that houses or receives the various components. Endoscopic member 74 includes a distal end 76 that is positioned by the physician proximate to the region of implantation. Distal end 76 may include a blunt tip 78 that provides an atraumatic surface and that protects the tissues of the patient upon insertion of distal end 76 into the body of the patient. As will be described below, distal end 76 may include an inflatable balloon to assist with positioning of distal end 76 in the body of a patient.

Distal end 76 also includes a lateral recess or cavity 80 to capture tissue such as the wall of a urethra proximate to the site of implantation. Cavity 80 serves for positioning and implantation of bulking prosthesis 72, as described below. Cavity 80 includes a plurality of vacuum ports 82, which may be coupled to a source of vacuum pressure through the body of endoscopic member 74. Overtube 74 may include a coupling element (not shown) to couple delivery apparatus 70 to a source of vacuum pressure.

In FIG. 4, distal end 76 has been rotated to make cavity 80 and vacuum ports 82 visible. Cavity 80 defines a substantially rectangular orifice or recess with a major axis extending longitudinally relative to endoscopic member 74. Other shapes for cavity 80 are possible, however. In general, cavity 80 is sized and shaped to permit capture of a selected amount of urethral wall to facilitate implantation of bulking prosthesis 52 in the tissues surrounding the urethra. For example, cavity 80 may have different dimensions for implantation of bulking prostheses of different dimensions.

A sheath assembly 86 couples to endoscopic member 74. Sheath assembly 86 includes a sheathe 88 that receives one or more tools that are inserted into the body of the patient through endoscopic member 74. One tool that can be received in sheath 88 is a needle assembly 90. The distal end of needle assembly 90 includes a needle 92, which can penetrate and make a hole in a wall of a urethra. In one embodiment of the invention, needle 92 is able to extend at an angle from distal end 76, to penetrate a wall of a urethra.

Another tool that can be received in sheath 88 is pushrod assembly 94. When bulking prosthesis 72 is inserted into sheath 88, pushrod assembly 94 drives bulking prosthesis 72 to the distal end of sheath 88. In a typical application, a physician makes a hole with needle 92 in a urethral wall proximate to a urethral sphincter, and pushes bulking prosthesis 72 through the hole with pushrod assembly 94.

Figure 5:
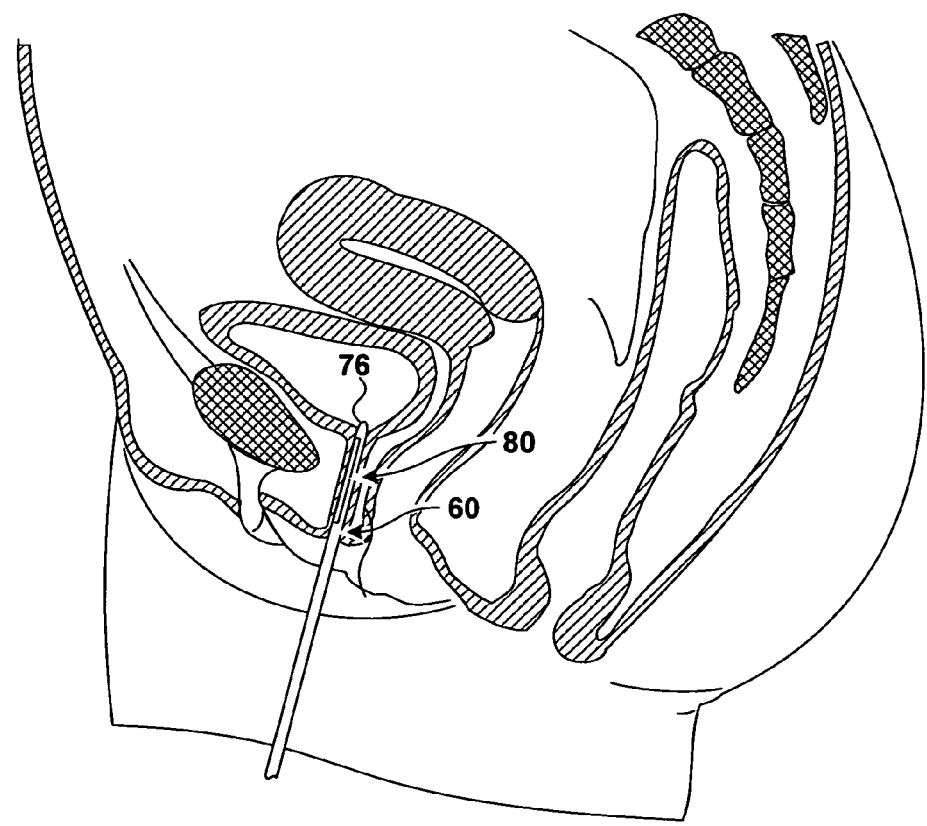
FIG. 5 is a sagittal cross section of an genitourinary region of a female patient, showing a technique for implantation of a bulking prosthesis with a delivery apparatus such as the delivery apparatus shown in FIG. 4.

FIG. 5 is a sagittal cross-section of genitourinary region of a female patient, showing a technique for implantation of a bulking prosthesis with a device such as delivery apparatus 70 shown in FIG. 4. With the patient under general or local anesthesia, a physician inserts distal end 76 into urethra 60 proximate to the external urethral sphincter and applies vacuum pressure from a vacuum source. The vacuum pressure draws the wall of urethra 60 into cavity 80. With the urethral wall in cavity 80, a physician makes a hole with needle 92 in the wall and pushes bulking prosthesis 72 through the hole with pushrod assembly 94.

Figure 6:
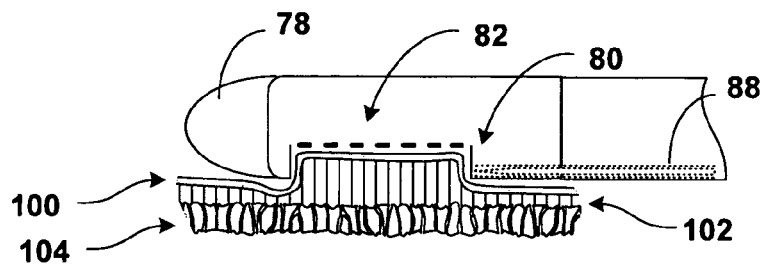
FIGS. 6-8 are side views of a delivery apparatus interacting with a urethral wall proximate to a urethral sphincter and implanting a bulking prosthesis, in a miniature state, in tissue proximate to the urethral sphincter.
Figure 7:
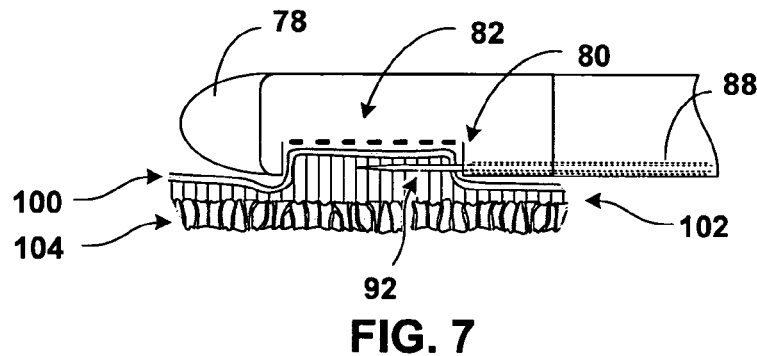
Figure 8:
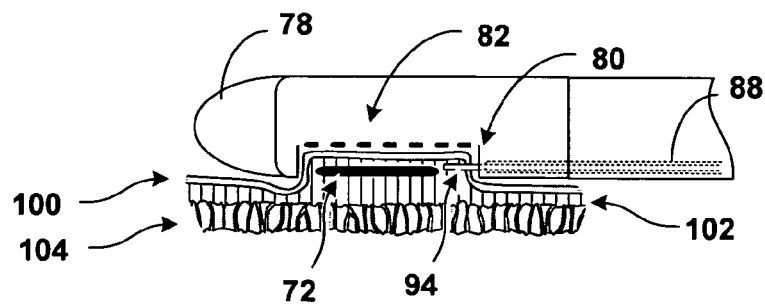

FIGS. 6-9 show a technique for implantation of a bulking prosthesis with a device as delivery apparatus 70. FIG. 6 depicts urethral wall 100 drawn into cavity 80 by vacuum pressure applied via vacuum ports 82. With urethral wall 100 in cavity 80, a physician makes a hole in wall 100 with needle 92, as shown in FIG. 7. The physician pushes needle assembly 90 through sheath 88, thereby making a hole in wall 100. Insertion of needle 92 through wall 100 causes needle 92 to form a pocket in the tissue 102 just outside the urethra. This pocket, which receives bulking prosthesis 72, may be enlarged by injection of fluid, such as a saline solution, into the tissue 102. The physician withdraws needle assembly 90 from sheath 88, and inserts bulking prosthesis 72 into sheath 88. The physician pushes bulking prosthesis 72 through the hole in wall 100 and into the pocket in tissue 102 with pushrod assembly 94, as shown in FIG. 8. When implanted, bulking prosthesis 72 is in a miniature state. Bulking prosthesis 72 is implanted in tissue 102 proximate to underlying musculature 104, which is typically the external urethral sphincter.

Figure 9:
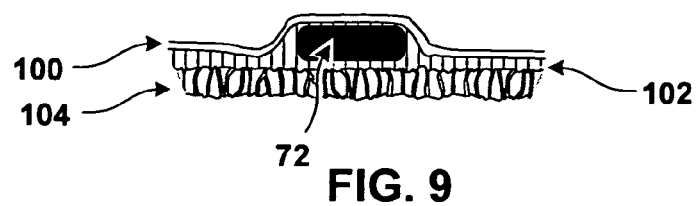
FIG. 9 is a view of a bulking prosthesis, in an enlarged state, implanted in tissue outside a urethra and proximate to a urethral sphincter.

As shown in FIG. 9, delivery apparatus 70 may be withdrawn following implantation. Over time, bulking prostheses 72 swells to an enlarged state, e.g., due to absorption of fluid from the body of the patient. With the extra bulk supplied by bulking prostheses 72 in its enlarged state, the patient can exercise voluntary control over the external urethral sphincter to close the urethra and maintain urinary continence. Delivery apparatus 70 can be employed to deliver one or more bulking prostheses of substantial size. As discussed below, the bulking prostheses may each have a long dimension (such as length or diameter) of two to twenty millimeters in the enlarged state.

Figure 10:
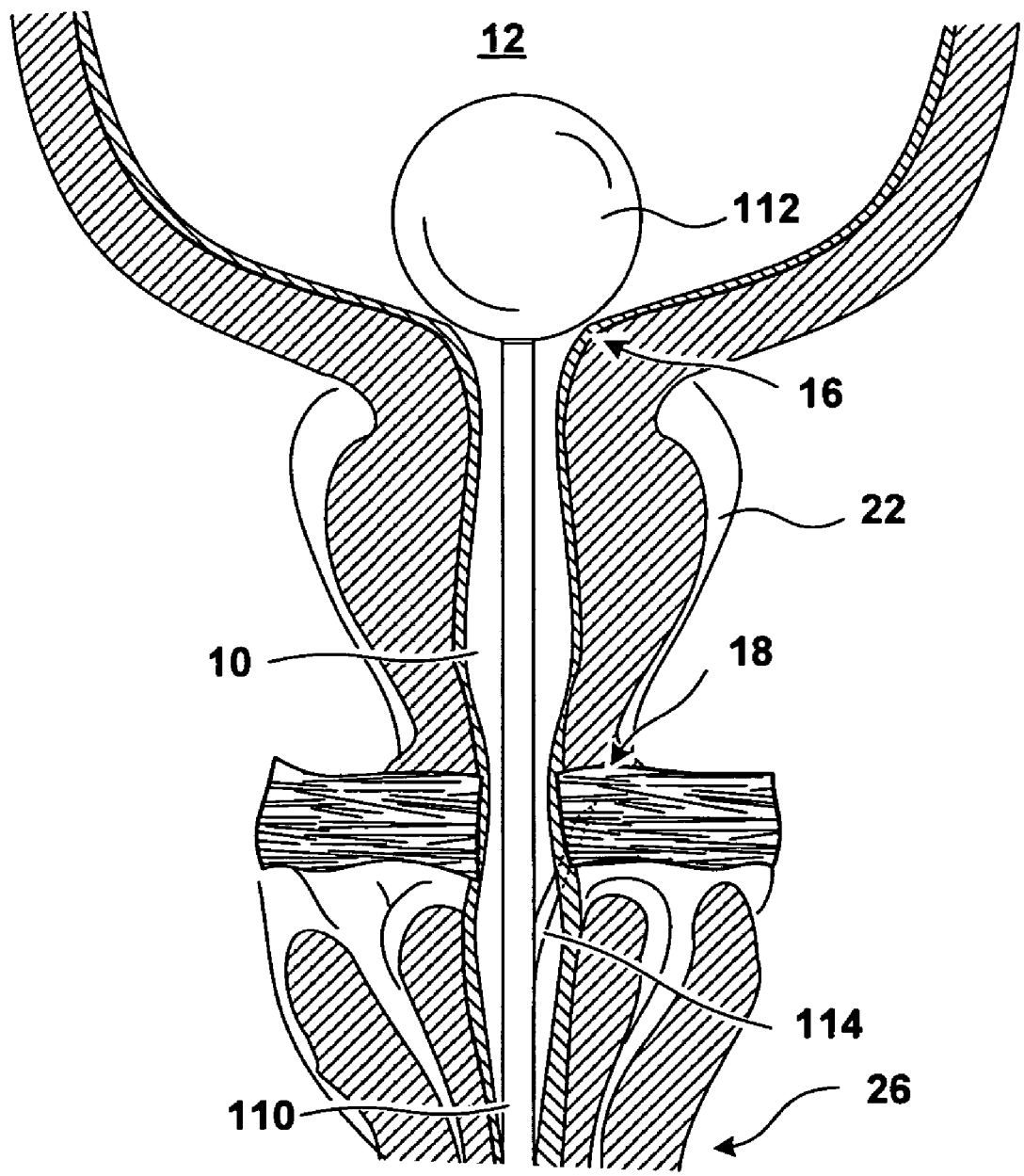
FIG. 10 is a coronal cross section of anatomical structures surrounding a urethra of a male patient, showing a technique for implantation of one or more bulking prostheses.

FIG. 10 is a coronal cross section of anatomical structures surrounding a urethra 10 of a male patient, showing a technique for implantation of a bulking prosthesis. The bulking prosthesis (not shown in FIG. 10) may be delivered with a delivery apparatus similar to delivery apparatus 90 shown in FIG. 4, but with modifications to enhance bulking prosthesis placement in males.

In particular, the distal end 110 of the delivery apparatus may be extended through penis 26 and into bladder 12. A balloon 112 in distal end 110 may be inflated, and the delivery apparatus may be withdrawn, leaving balloon proximate to internal urethral sphincter 16. In this way, bladder 12 serves as a landmark for placement of bulking prostheses.

A needle 114 may be extended from distal end 110 through the wall of urethra 10 and into the tissues outside urethra. A bulking prosthesis may be expelled into the tissues, either by pushing the bulking prostheses through the hole made by needle 114, or by ejecting the bulking prostheses from a lumen of needle 114.

A capsule-shaped bulking prosthesis, such as bulking prostheses 72 shown in FIG. 9, or a or substantially cylindrical bulking prosthesis, may have a diameter of two to ten millimeters when in the enlarged state. In a typical application, the diameter of the bulking prosthesis may be two to four millimeters. The length of the bulking prosthesis may be four to twenty millimeters in the enlarged state, with a length of ten to fifteen millimeters being typical.

The implantation techniques shown in FIGS. 2-10 need not be limited to capsule-shaped or substantially cylindrical bulking prostheses, however. A bulking prostheses may assume other shapes as well. A hydrogel spherical bulking prosthesis, for example may have a diameter of one-half to five millimeters in the enlarged state, with a diameter of one to three millimeters being typical. A hydrogel bulking prosthesis may also be for example, egg-shaped, with dimensions comparable to that of a spherical or capsule-shaped bulking prosthesis.

Figure 11:
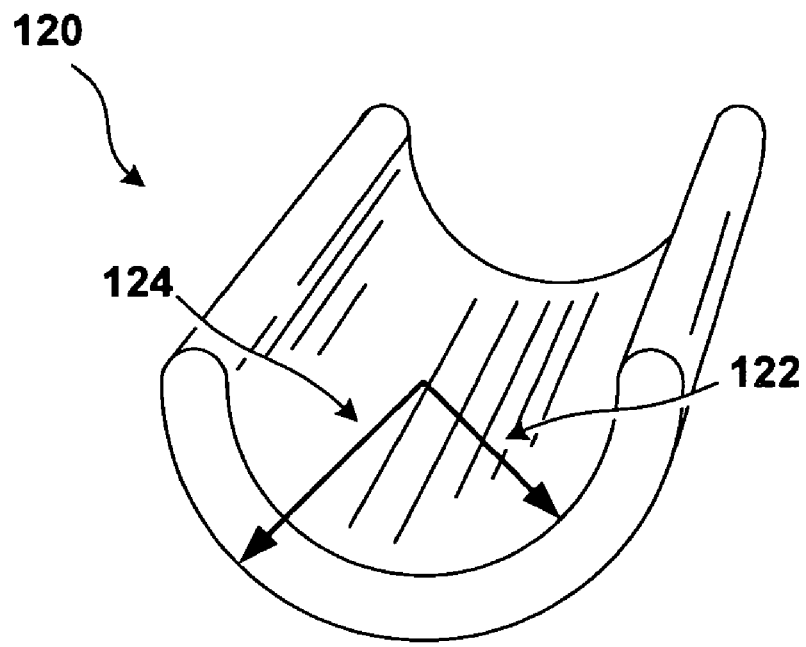
FIG. 11 is a perspective diagram of one embodiment of a bulking prosthesis in an enlarged state.
Figure 12:
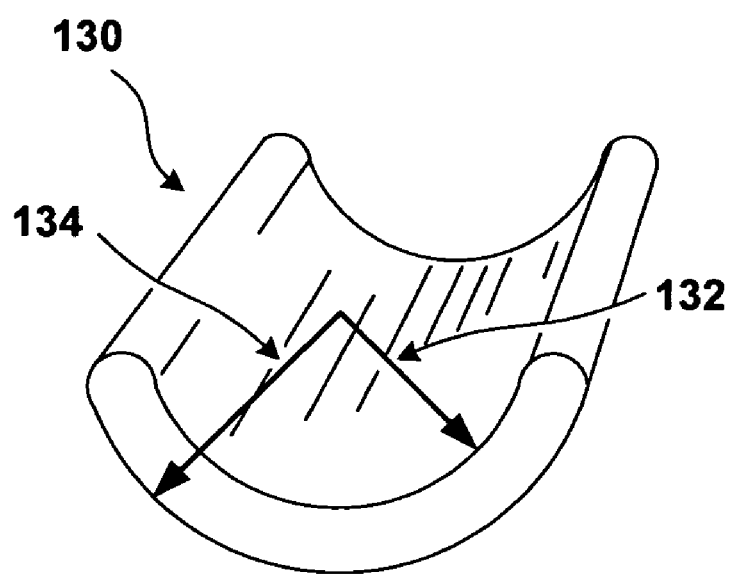
FIG. 12 is a perspective diagram of another embodiment of a bulking prosthesis in an enlarged state.

FIGS. 11 and 12 illustrate two other exemplary hydrogel bulking prostheses 120, 130. Bulking prostheses 120, 130 are shown in the enlarged state, and both are in the shape of a partial cylinder.

Bulking prosthesis 120 shown in FIG. 11 is substantially a half-cylinder, and has a C-shaped or "horseshoe" shaped cross-section. Bulking prosthesis 120 has an inner surface radius 122 that is sized to conform to close the urethra of the patient when the patient exercises voluntary control over the external urethral sphincter. Inner surface radius 122 is sized to the dimensions of the urethra of a particular patient, with a typical inner surface radius 122 being in the range of one-half to fifteen millimeters. The outer surface radius 124 of bulking prosthesis 120 is larger than inner surface radius 122 by about one-half to five millimeters. The length of bulking prosthesis 120 may range from two to twenty millimeters. The cross-section of bulking prosthesis 120 need not be uniform, and bulking prosthesis 120 may resemble a curved wedge.

In a typical implantation, two half-cylinder bulking prostheses like bulking prosthesis 120 may be implanted in a patient on opposite sides of the urethra. The two prostheses would not be coupled to one another, but their inner surfaces would be coaxial with the urethra of the patient. When the patient exercises voluntary control over the external urethral sphincter, the bulking prostheses supply the bulk to close the urethra. When the patient needs to urinate, however, the patient can relax the external urethral sphincter and allow the bulking prostheses to separate from one another, allowing the urethra to open and urine to pass.

Bulking prosthesis 130 shown in FIG. 12 is a partial cylinder, and is less than a half-cylinder. Like bulking prosthesis 120, bulking prosthesis 130 has a C-shaped cross-section and an inner surface radius 132 that is sized to conform to close the urethra of the patient when the patient exercises voluntary control over the external urethral sphincter. In a typical implementation, inner surface radius 132 may be in the range of one-half to fifteen millimeters, and the outer surface radius 134 of bulking prosthesis 130 may be larger than inner surface radius 132 by about one-half to five millimeters. The length of bulking prosthesis 100 may range from two to twenty millimeters.

In a typical implantation, three or four bulking prostheses like bulking prosthesis 130 may be implanted in a patient around the urethra. The inner surfaces of the prostheses would be coaxial with the urethra of the patient. When the patient exercises voluntary control over the external urethral sphincter, the bulking prostheses supply the bulk to close the urethra. When the patient needs to urinate, however, the patient can relax the external urethral sphincter and allow the bulking prostheses to separate from one another, allowing the urethra to open and urine to pass.

Bulking prostheses 120 and 130 in FIGS. 11 and 12, when in a miniature state, need not be C-shaped. Rather, the prosthesis may be curled or folded to slide inside a needle such as needle 38 in FIG. 2 or needle 114 in FIG. 10, or a catheter or sheathe such as sheathe 88 in FIG. 4.

The invention may provide one or more advantages. Initial treatments for urinary incontinence tend to be conservative treatments, such as having the patient perform exercises to strengthen the external urethral sphincter. If the conservative treatments are unsuccessful, however, surgical intervention may be indicated. The invention provides for less invasive surgical intervention than other surgical techniques. As a result, the implantations may be performed in less time and with less expense, and with reduced recovery time for the patient. In addition, bulking prostheses implanted according to the invention may be readily removed, if necessary.

Once the implants are in place, no further maintenance is necessary. Unlike some urinary incontinence therapies, there is no need for an electrical supply, and there are no coupled moving parts. The dimensions and shapes of the bulking prostheses help promote continence and resist breakage and migration.

Various embodiments of the invention have been described. Various modifications can be made to the described embodiments without departing from the scope of the invention. For example, the bulking prostheses may include a textured or porous surface to enhance stabilization or fixation. In one embodiment, a hydrogel bulking prosthesis may include a textured surface, and in another embodiment, the hydrogel may be enclosed in a layer of porous material, such as Dacron mesh.

The dimensions of the bulking prostheses are for illustration, and the invention is not limited to the ranges of dimensions provided above. Nor is the invention limited to the shapes described specifically above. The invention encompasses implantation techniques in addition to those described above. The invention further encompasses implantation of multiple prostheses at a single time, e.g., by implantation of two or more spherical bulking prostheses through the lumen of a syringe needle. These and other embodiments are within the scope of the following claims.

The invention claimed is:

1. A method for treating urinary incontinence comprising:
   applying vacuum pressure to an instrument proximate to a urethral wall of a patient to draw a portion of the urethral wall into a cavity in the instrument;
   forming a hole in the portion of the urethral wall disposed in the cavity; and
   implanting a bulking prosthesis through the hole at the external urethral sphincter, wherein said bulking prosthesis does not migrate after said implanting and said bulking prosthesis allows the patient to exercise voluntary control over said external sphincter.

2. The method of claim 1, wherein the bulking prosthesis is in a miniature state at the time of implantation and assumes an enlarged state after implantation.

3. The method of claim 1, wherein forming the hole comprises forming the hole with a needle having a lumen, and wherein implanting the bulking prosthesis comprises pushing the bulking prosthesis through the lumen in the needle.

4. The method of claim 1, wherein the bulking prosthesis comprises a hydrogel.

5. The method of claim 1, wherein the bulking prosthesis comprises a material that absorbs fluid to assume the enlarged state.

6. A system comprising:
- a tubular instrument having a distal end and sized for introduction into a urethra of a patient, the distal end including a cavity;
- a vacuum port to draw a portion of a urethral wall of the patient into the cavity;
- a needle to make a hole through the urethral wall in the portion of the urethral wall disposed in the cavity; and
- a pushing agent to push a bulking prosthesis through the tubular instrument and through the hole in the urethral wall,
- wherein the distal end of the tubular instrument includes an inflatable balloon to assist with positioning of the distal end in the body of the patient.

7. The system of claim 6, further comprising:
- a source of vacuum pressure; and
- a conduit to deliver the vacuum pressure from the source to the urethral wall.

8. The system of claim 6, wherein the tubular instrument comprises the needle.

9. The system of claim 6, wherein the tubular instrument comprises a cystoscope.

10. The system of claim 6, wherein the bulking prosthesis has a partial cylinder shape with a substantially C-shaped cross-section and an inner surface radius.

11. The system of claim 10, wherein the inner surface radius is sized to conform to close the urethra when the patient exercises voluntary control over an external urethral sphincter of the patient.

12. The system of claim 11, wherein the bulking prosthesis comprises a first bulking prosthesis and a second bulking prosthesis, each of the first and second bulking prosthesis comprising the partial cylinder shape with the substantially C-shaped cross section, the first and second bulking prosthesis being implantable proximate to the external urethral sphincter on opposite sides of the urethra of the patient.

13. The system of claim 12, wherein the partial cylinder shape is substantially a half cylinder shape.

\* \* \* \* \*

UNITED STATES PATENT AND TRADEMARK OFFICE
CERTIFICATE OF CORRECTION

PATENT NO. : 7,585,271 B2 Page 1 of 1
APPLICATION NO. : 10/698131
DATED : September 8, 2009
INVENTOR(S) : Gerber et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 891 days.

Signed and Sealed this

Fourteenth Day of September, 2010

David J. Kappos
*Director of the United States Patent and Trademark Office*